United States Patent [19]

Fitzpatrick

[11] Patent Number: 4,897,497
[45] Date of Patent: Jan. 30, 1990

[54] LIGNOCELLULOSE DEGRADATION TO FURFURAL AND LEVULINIC ACID

[75] Inventor: Stephen W. Fitzpatrick, Framingham, Mass.

[73] Assignee: Biofine Incorporated, Wilmington, Del.

[21] Appl. No.: 186,234

[22] Filed: Apr. 26, 1988

[51] Int. Cl.$^4$ .................. C07D 307/48; C07D 307/50
[52] U.S. Cl. ..................................... 549/489; 549/490; 562/515
[58] Field of Search .......................................... 549/489

[56] References Cited

U.S. PATENT DOCUMENTS

| | | | |
|---|---|---|---|
| 3,258,481 | 6/1966 | Sassenrath et al. | 562/515 |
| 3,701,789 | 10/1972 | Ramos-Rodriguez | 549/489 |
| 4,237,226 | 12/1980 | Grethlein | 435/99 |
| 4,469,524 | 9/1984 | Assarsson et al. | 127/28 |
| 4,497,896 | 2/1985 | Assarsson et al. | 435/161 |
| 4,578,353 | 3/1986 | Assarsson et al. | 435/161 |

OTHER PUBLICATIONS

Thomas et al., "Biomass Derived Levulinic Acid Derivatives and Their Use as Liquid Fuel Extenders", pp. 333–348.

Kwarteng, Abstract (Thayer School of Engineering), "Kinetics of Acid Hydrolysis of Hardwood in a Continuous Plug Flow Reactor", (7/83).

*Primary Examiner*—Morton Foelak
*Assistant Examiner*—Frederick Krass

[57] ABSTRACT

A process for producing furfural and levulinic acid from lignocellulose includes subjecting a sample of lignocellulose to acid degradation at an elevated temperature for a minute or less, during which time at least fifty percent of the furfural that theoretically can be derived from the sample is generated. The resulting mixture is then subjected to a second acid degradation at an elevated temperature to produce levulinic acid. During the second acid degradation, furfural vapors are continuously collected from the mixture.

27 Claims, 1 Drawing Sheet

LIGNOCELLULOSE DEGRADATION TO FURFURAL AND LEVULINIC ACID

BACKGROUND OF THE INVENTION

This invention relates to processes for producing furfural and levulinic acid from lignocellulose.

Lignocellulose consists of cellulosic polymers bound together by lignin. When subjected to acid treatment, lignocellulose splits into lignin and a cellulosic component; the cellulosic component can then hydrolyze to its constituent pentose and hexose monomers. The pentose monomers, upon further acid treatment, can degrade to furfural, and the hexose monomer can degrade to hydroxymethylfurfural. Hydroxymethylfurfural can degrade still further in the presence of acid to levulinic acid.

Furfural is used primarily in lubricating oil manufacture and in making resins. Levulinic acid is also used to make resins, and, in addition, plasticizers, fragrance products, and pharmaceuticals. Lignin is used in making vanillin and as a filler and binder in some resin products.

SUMMARY OF THE INVENTION

In general the invention features a process for producing furfural and levulinic acid from lignocellulose. According to the process a sample of lignocellulose is subjected to acid degradation at an elevated temperature for a minute or less, during which time at least fifty percent of the furfural that theoretically can be derived from the sample is generated. The resulting mixture is then subjected to a second acid degradation at an elevated temperature to produce levulinic acid. During the second acid degradation, furfural vapors are continuously collected from the mixture.

Good yields of both furfural and levulinic acid are efficiently produced in the featured process. Furfural is generated quickly in the first stage of the process and is separated rapidly as a vapour and collected as a condensate after separation in the second stage, thus preventing decomposition of the generated furfural.

In some preferred embodiments the levulinic acid is also continuously collected as it is generated, most preferably by drawing off the liquids (including levulinic acid) from the second stage. In addition lignin, which also has been generated, may also be collected, e.g., by filtration of the liquids from the final reaction mixture. The lignin is obtained in high yield and is of a high grade, i.e., relatively sulfur-free, chemically uncondensed, alkali-soluble, and easily-filtered.

In other preferred embodiments the initial acid degradation step is carried out in a first tubular reactor that includes an entrance and an exit between which volumes of the sample pass without significant axial mixing; and the later acid degradation step is carried out in a second reactor having an entrance connected to the exit of the first reactor. The process further includes, when this system is employed, continuously supplying a volume of the sample to the first reactor, and continuously removing a corresponding volume of the mixture generated from the first reactor and supplying that volume to the second reactor. Preferably a sulfite salt (e.g., sodium or potassium sulfite) is added to the sample to prevent clogging of the first reactor. Using a two reactor continuous system in which the products (furfural and levulinic acid) are continuously collected provides an efficient use of equipment and space, as large quantities of the sample can be run through a relatively small system, and the products collected, in a short time. The lack of axial mixing in the first reactor ensures that a given portion of the sample does not spend too much time in the first reactor.

The system can also be operated with a continuous first stage and a "batch-type" second stage. In addition, the second stage can be operated continuously as a distillation or stripping column, thus ensuring efficient collection of furfural from the degradation mixture.

In other embodiments, the most preferred acid degradation conditions are used. For the initial acid degradation step, these conditions include a temperature of 210–250° C., a reaction time of 7–30 seconds, and an acid weight of 2–7% the weight of the sample (aqueous portion). For the second acid degradation step, these conditions include a temperature of 150–200° C.; an average reaction time of 1–30 minutes; and an acid weight of 3–10% the weight of the sample (aqueous portion).

Other features and advantages of the invention will be apparent from the following description of the preferred embodiment thereof, and from the claims.

DESCRIPTION OF THE PREFERRED EMBODIMENT AND BRIEF DESCRIPTION OF DRAWINGS

Figure 1:
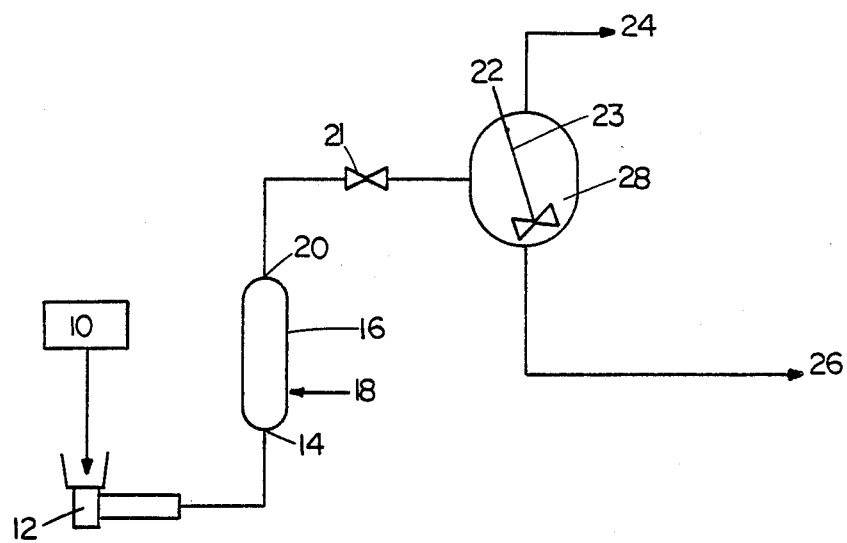

The FIG. is a flow diagram illustrating the steps of a preferred process.

Referring to the Figure, an aqueous acidified slurry 10 consisting of ground wood or other lignocellulose sample in dilute mineral acid (e.g., HCl; HBr; $H_2PO_4$; $H_2SO_4$) is pumped by a high pressure pump 12 into an entrance 14 of a tubular reactor 16. The temperature in the reactor is maintained at an elevated level by the injection of high pressure steam 18; the pressure in the reactor is maintained at a sufficient level to give rapid condensation of the steam and to prevent the reactor contents from vaporizing. The lignocellulose is degraded by the acid as the mixture passes through reactor 16. The mixture flows in the axial direction; there is no axial mixing of the mixture as it passes through the reactor. The mixture flows out of the reactor through an exit 20.

The slurry should consist of 5–25% ground wood (or other suitable lignocellulose sample) by weight. The use of larger amounts of ground wood can lead to the clogging of reactor 16.

While in reactor 16 the lignocellulose is degraded by the acid to lignin and the constituent pentose and hexose monomers of cellulose. Pentose monomers are further degraded to furfural, and hexose monomers are further degraded to hydroxymethylfurfural, the levulinic acid precursor. The conditions (temperature; residence time; quantity of acid) in reactor 16 are selected so that at least 50% (more preferably at least 60% and most preferably at least 75%) of the theoretical amount of furfural that can be derived from the lignocellulose in the sample is generated, in as short a time as possible (at most, a minute). Less than 10% (generally less than 3%) of the theoretical amount of levulinic acid that can be derived from the sample is generated.

The temperature in the first reactor preferably is 180–265° C. (more preferably 210–250° C.). If the temperature is too low, the acid degradation will not proceed at a fast enough rate. If the temperature is too high, too much pressure may be generated in the reactor and also, the first stage degradation may proceed too quickly.

The slurry preferably includes 1–10% (more preferably 2–7%) mineral acid by weight of the aqueous portion of the slurry. If too much acid is used, there may be corrosion problems with the equipment and also, the first stage degradation may proceed too quickly. If too little acid is used, the degradation will not proceed at a fast enough rate.

The amount of time the lignocellulose spends in the reactor 16 should be 3–60 seconds (more preferably, 7–25 seconds). The lignocellulose needs to have sufficient time to properly degrade, but the degradation products should not be exposed to elevated temperatures for an extended period or substantial unwanted decomposition of the products may occur.

One skilled in the art will recognize that the above conditions are interrelated. Thus, the higher the temperature used, the shorter the residence time and the lower the acid concentration needed to obtain the targeted level of degradation. Similarly, the lower the residence time used the higher the acid concentration and the higher the temperature needed.

To prevent clogging of the tubular reactor 16, a sulfite salt is preferably added to the slurry. Anywhere from 2–200 ppm of the sulfite salt by weight should be used. Too little sulfite salt has insufficient effect, too much causes adverse reactions at high temperatures.

The reaction mixture flows from reactor 16, through a pressure reduction valve 21, and into a tank-type reactor 22, which can be equipped with a stirrer 23 to improve mixing. Because the pressure in the second reactor is lower than in the first reactor the temperature will be lower, although an elevated temperature is still maintained; the temperature is controlled by adjusting the pressure in the continuous mode and by adjusting heat input in the batch mode.

The temperature, mineral acid concentration, and average residence time of a volume of the mixture in the second reactor when operated continuously are selected so that the remaining pentose monomers, if any, are converted to furfural; the remaining hexose monomers, if any, are converted to hydroxymethylfurfural molecules; and the hydroxymethylfurfural molecules are further degraded to levulinic acid. In addition, the conditions are adjusted so that any furfural present vaporizes quickly. The furfural vapor 24 produced exits the reactor 22 and is externally condensed. The levulinic acid, which is a liquid at the conditions used in the second stage reactor, settles to the bottom of the reactor 22 with other liquids, and can be continuously drawn off in liquid stream 26. For a given time period the volume of furfural and levulinic acid removed from the reactor 22 should equal the volume of the reaction mixture added to the reactor 22 from the first reactor 16. Lignin leaves the second reactor 22 in stream 26 and can be removed by filtration. In the batch operating mode following completion of the degradation of a selected amount of the sample, the reactors are allowed to cool, and the mixture in the reactor 22 is filtered to collect high grade lignin.

The temperature in the reactor 22 preferably should be 130–250° C. (more preferably 150–200° C.). If the temperature is too high substantial, unwanted, decomposition of the components of the mixture may occur. If the temperature is too low the conversion of hydroxymethylfurfural and other intermediate compounds to levulinic acid may be too slow. The average residence time a given volume of the mixture from the first reactor 16 remains in the reactor 22 should be 1–60 minutes (more preferably 2–30 minutes). Average residence time, as used herein, refers to the time it takes to remove from the reactor (by the draining of the liquid components such as levulinic acid) a volume of components of the mixture equal to the average volume of the mixture in the reactor 22. If the average residence time is too short, the degradation to the desired products may not be complete. If the average residence time is too long the efficiency of the system is diminished.

The mineral acid concentration of the aqueous portion of the mixture in the reactor 22 preferably is 1–15% (more preferably 3–10%) by weight. The mineral acid concentration can be adjusted upward at this stage, if desired, by adding acid to the mixture entering the reactor. If the acid concentration is too high, corrosion of the equipment and, possibly, unwanted decomposition of the components of the mixture may occur. If the acid concentration is too low, the production of levulinic acid may be too slow.

As with the conditions used in the first reactor, one skilled in the art will recognize that the conditions used in the second reactor are interrelated.

The following are examples of the process.

EXAMPLE 1

46.1 lbs. per hour dry ground hardwood were mixed continuously into hot water and the resulting 0 slurry pumped continuously through a 2 inch diameter tubular reactor using a multistage high pressure screw pump. The reactor temperature was maintained at 214.8° C. by continuous injection of high pressure steam. Before entering the reactor the wood slurry was acidified with sulphuric acid to an acid concentration of 7.5% of the weight of the aqueous portion of the slurry. The average residence time in the reactor was 12 seconds. The reactor was continuously discharged through a pressure reducing valve into a continuous second stage tank reactor which was held at 185° C. by continuously controlling the outlet pressure of the vapor stream leaving the top of the tank reactor. Furfural present in the vapour stream from this second stage reactor was condensed. The liquid stream continuously leaving the second stage contained levulinic acid. The residence time of the liquid in the second stage was 2 minutes and the acidity was approximately 8.5% of the weight of the liquid. The yield of furfural obtained by analysis of the outlet streams was 84.3% of theoretical (molar yield based on the pentose polymer content of the wood feed). The yield of levulinic obtained by analysis of the liquid outflow from the second stage reactor was 30% of theoretical (molar yield based on the hexose polymer content of the wood feed). A sodium sulphite concentration of 100 ppm was maintained in the system by addition of sulphite in the acid feed to prevent reactor blockage with degradation products.

EXAMPLE 2

46.1 lbs per hour dry ground wood (hardwood) are mixed continuously into hot water and the resulting slurry pumped continuously through a 2 inch diameter tubular reactor using a multistage high pressure screw pump The reactor temperature was maintained at 213.8° C. by continuous injection of high pressure steam. Before entering the reactor the wood slurry was acidified with sulphuric acid to an acid concentration of 7.5% of the weight of the aqueous portion of the slurry. The average residence time in the reactor was 12 seconds. The reactor was continuously discharged through a pressure reducing valve into a receiver tank which allowed the furfural to vaporize and leave from the top of the vessel. Furfural vapours were condensed and collected. A sample of the liquid outflow from this receiver tank was cooked batch-wise without further acidification at 185° C. for 45 minutes in a stirred pressurized reactor. The levulinic acid yield obtained by analysis of the liquors from this batch reaction was 55% of theoretical (molar yield based on hexose polymer content of wood feed). The furfural yield obtained by analysis of the outlet streams from the receiver tank was 83.5% of theoretical (molar yield based on pentose polymer content of the wood). A concentration of 100 ppm sulphite (sodium salt) was maintained in the reactor system by addition of the salt to the sulphuric acid feed to prevent reactor blockage with degradation products.

EXAMPLE 3

53.75 lbs per hour dry ground wood (hardwood) were mixed continuously into hot water and the resulting slurry pumped continuously through a 2 inch diameter tubular reactor using a multistage high pressure screw pump. The reactor temperature was maintained at 221.5° C. by continuous injection of high pressure steam. Before entering the reactor the wood slurry was acidified with sulphuric acid to an acid concentration of 3.7% by weight of the aqueous portion of the slurry. The average residence time in the reactor was approximately 10 seconds (this being reduced partially by tar laydown in the reactor). The reactor was continuously discharged through a pressure reducing valve into a continuous second stage tank. This tank allows furfural vapours to be taken overhead and condensed. The liquid stream was maintained at 200° C. for 30 minutes (no further acid addition). The furfural yield obtained (calculated as before) was 73.6% of theoretical and the levulinic acid yield obtained was 48.8% of theoretical.

In calculation of the yields in all of the preceding examples the theoretical maximum weight yield of furfural is calculated as 72.7%, (the ratio of the molecular weight of furfural (96) divided by the molecular weight of the basic unit of the pentose polymer (132)). For levulinic acid the maximum theoretical weight yield is 71.6% (the ratio of molecular weights of levulinic acid (116) and hexose polymer (162)).

In all of the above examples the feed was mixed hardwood. The percentage of hexose, pentose polymers and lignin is as follows (measured by chemical analysis of the dry samples).

| | | |
|---|---|---|
| hexose polymer | 44% | (by weight) |
| pentose polymer | 19% | |
| lignin | 24% | |
| others | 13% | |
| total | 100% | |

Other embodiments are within the following claims.

I claim:

1. A process for producing furfural and levulinic acid from lignocellulose, said method comprising
   (1) in a first reactor having an entrance and an exit, subjecting a sample comprising lignocellulose to acid degradation at an elevated temperature for a time less than a minute to yield a degradation mixture comprising at least fifty percent of the furfural that theoretically can be derived from said sample;
   (2) continuously supplying a volume of said sample to said first reactor through said entrance of said first reactor and continuously removing through said exit of said first reactor a corresponding volume of said degradation mixture and supplying said corresponding volume to a second reactor;
   (3) in said second reactor, subjecting said degradation mixture to further acid degradation at elevated temperature to produce levulinic acid; and
   (4) during step (3), continuously collecting furfural from said degradation mixture by condensation of furfural vapors arising from said mixture.

2. The process of claim 1 further comprising continuously collecting levulinic acid from said degradation mixture during step (3).

3. The process of claim 2 wherein said levulinic acid is collected by drawing off liquids containing levulinic acid from said degradation mixture.

4. The process of claim 1 wherein said degradation mixture further comprises lignin, said method further comprising collecting said lignin from said degradation mixture.

5. The process of claim 1 wherein step (1) is carried out in a first reactor having an entrance and an exit and step (3), is carried out in a second reactor having an entrance connected with said exit of said first reactor, said method further comprising continuously supplying a volume of said sample to said first reactor through said entrance of said first reactor and continuously removing through said exit of said first reactor a corresponding volume of said degradation mixture and supplying said corresponding volume to said second reactor.

6. The process of claim 1 wherein said first reactor is a tubular reactor and said sample is passed through said tubular reactor without significant axial mixing.

7. The process of claim 1, further comprising mixing said degradation mixture in said second reactor.

8. The process of claim 1 further comprising adding a sulfite salt to said sample to prevent clogging of said first reactor.

9. The process of claim 1 wherein in step (1) said sample is subjected to acid degradation for at least three seconds.

10. The process of claim 9 wherein in step (1) said sample is subjected to acid degradation for between 7 and 30 seconds.

11. The process of claim 1 wherein in step (1) said elevated temperature is between 180° C. and 265° C.

12. The process of claim 11 wherein in step (1) said elevated temperature is between 210° C. and 250° C.

13. The process of claim 1 wherein in step (1) the aqueous portion of said sample comprises 1 to 10% by weight mineral acid.

14. The process of claim 13 wherein in step (1) said aqueous portion of said sample comprises 2 to 7% by weight mineral acid.

15. The process of claim 1 wherein in step (3) said degradation mixture is subjected to acid degradation for an average time of between 1 and 60 minutes.

16. The process of claim 15 wherein in step (3) said degradation mixture is subjected to acid degradation for an average time of between 2 and 30 minutes.

17. The process of claim 1 wherein in step (3) said elevated temperature is between 130° C. and 250° C.

18. The process of claim 17 wherein in step (3) said elevated temperature is between 150° C. and 200° C.

19. The process of claim 1 wherein in step (3) the aqueous portion of said degradation mixture comprises 1 to 15% by weight mineral acid.

20. The process of claim 19 wherein in step (3) said aqueous portion of said degradation mixture comprises 3 to 10% by weight mineral acid.

21. The process of claim 1 wherein in step (1) said elevated temperature is between 210° C. and 250° C.; said sample is subjected to acid degradation for between 7 and 30 seconds; and said sample comprises 2 to 7% by weight mineral acid.

22. The process of claim 21 wherein in step (3) said elevated temperature is between 150° C. and 200° C.; said degradation mixture is subjected to acid degradation for an average time of between 2 and 30 minutes; and the aqueous portion of said degradation mixture comprises 3 to 10% by weight mineral acid.

23. The process of claim 1 wherein in step (3) said elevated temperature is between 150° C. and 200° C.; said degradation mixture is subjected to acid degradation for an average time of between 2 and 30 minutes; and the aqueous portion of said degradation mixture comprises 3 to 10% by weight mineral acid.

24. The process of claim 1 wherein in step (1) said degradation mixture comprises at least sixty percent of the furfural that theoretically can be derived from said sample.

25. The process of claim 24, wherein in step (1) said degradation mixture comprises at least seventy-five percent of the furfural that theoretically can be derived from said sample.

26. The process of claim 1 wherein said degradation mixture from step (3) contains at least 30% of the levulinic acid that theoretically can be derived from said sample.

27. The process of claim 26 wherein said degradation mixture from step (3) contains at least 55% of the levulinic acid that theoretically can be derived from said sample.

* * * * *